US005334178A

United States Patent [19]

Haber et al.

[11] Patent Number: 5,334,178

[45] Date of Patent: Aug. 2, 1994

[54] PIERCEABLE PHARMACEUTICAL CONTAINER CLOSURE WITH CHECK VALVE

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 47,326

[22] Filed: Apr. 14, 1993

[51] Int. Cl.[5] ........................ A61B 19/00; A61M 5/32

[52] U.S. Cl. .................................... 604/415; 604/403; 604/407; 604/905; 604/324

[58] Field of Search .................... 128/912; 604/86-90, 604/201-204, 236-237, 321, 323-324, 403, 407, 415, 905

[56] References Cited

U.S. PATENT DOCUMENTS

| | | | |
|---|---|---|---|
| 2,851,201 | 9/1958 | Poitras et al. | 604/407 |
| 4,863,453 | 9/1989 | Berger et al. | 604/415 |
| 5,067,948 | 11/1991 | Haber et al. . | |
| 5,188,628 | 2/1993 | Rani et al. | 604/415 |

*Primary Examiner*—Randall L. Green
*Assistant Examiner*—P. Zuttarelli
*Attorney, Agent, or Firm*—Townsend and Townsend Khourie and Crew

[57] ABSTRACT

A pharmaceutical container comprises a housing with a wall structure and bottom defining an inner volume, a pierceable diaphragm sealingly positioned within an opening in the housing, and a protective cover received over the diaphragm. The diaphragm has at least one fluid check valve integrally formed therein and affording one way fluid communication from ambient toward the inner volume of the housing when the fluid pressure inside the container is less than ambient. The protective cover has one or more openings in fluid communication with the diaphragm check valves either via a set of grooves formed in the upper surface of the diaphragm or through a path provided by a spacer positioned between the cover and the diaphragm. A tear away seal covers the holes in the cover to prevent air flow toward the check valves prior to initial use. When the diaphragm is pierced by a syringe needle and the syringe plunger is withdrawn, air flows from ambient through the check valves into the inner volume of the container, thereby preventing suction on the liquid flowing through the needle into the syringe.

20 Claims, 9 Drawing Sheets

*fig.* 11

PIERCEABLE PHARMACEUTICAL CONTAINER CLOSURE WITH CHECK VALVE

BACKGROUND OF THE INVENTION

This invention relates to pharmaceutical containers of the type having a pierceable diaphragm to permit dispensing of a pharmaceutical from the container into a syringe.

Modern medical and pharmaceutical practices rely in part on the availability of liquid medication which is frequently presented in a pharmaceutical container. Typically, the container is provided with a pierceable diaphragm covered by a rupturable or removable seal. The diaphragm is designed to permit withdrawal of the liquid from the container by inserting a hollow needle through the diaphragm. The liquid is withdrawn through the needle and into a syringe for subsequent injection into a patient or into a pharmaceutical delivery device, such as an intravenous bag. In some applications, containers of the type having a pierceable diaphragm are multi-use containers: i.e., capable of holding more than a single dose. In such applications, the diaphragm is fabricated from a self-healing material, such as butyl rubber, so that the diaphragm can accept repeated piercing by a needle for withdrawal of appropriate aliquots.

Both unit dose and multi-dose containers are typically presented free of any pressure differential between the inner volume and ambient. As a consequence, the contents of the container are normally at ambient pressure. To withdraw liquid medication, the user initially places back pressure on a plunger of a syringe to entrain air into the syringe. Next, the seal is broken or removed, and the needle attached to the syringe is introduced into the inner volume of the container through the pierceable diaphragm. Next, air in the syringe is injected into the container by applying forward pressure on the syringe plunger, which temporarily increases the fluid pressure inside the container. Next, the plunger is withdrawn while maintaining the tip of the needle immersed in the liquid medication. The temporarily increased pressure inside the container assists in withdrawing the liquid medication easily and smoothly. When the desired amount of liquid medication has been withdrawn, the needle is removed from the diaphragm. This technique suffers from the disadvantage that the temporarily increased pressure within the container diminishes as the liquid medication is withdrawn, thereby providing reduced fluid pressure assistance for the flowing medication. In addition, if too much air is injected initially, the diaphragm can be forcibly ejected along with a portion of the medication. For those medications which are highly caustic, this can result in accidental injury to the user.

A less preferred alternative for withdrawing liquid medication from a pharmaceutical container of the pierceable diaphragm type consists of omitting the initial injection of air into the container to pressurize the inner volume and proceeding directly to the step of withdrawing the desired amount of liquid medication by applying back pressure on the syringe plunger. This technique suffers from the disadvantage of creating a pressure differential between the container interior and ambient, with the pressure inside the container lower than ambient pressure. This causes the pierceable diaphragm to be increasingly drawn inwardly of the container as the liquid medication is progressively withdrawn. For a multi-dose container, repeated forcible flexing of the diaphragm caused by creation of the pressure differential and the relaxation thereof when the needle is withdrawn can compromise the integrity of the diaphragm, particularly at those points where the diaphragm attaches to the confronting surfaces of the container. In addition, this technique suffers from the disadvantage of requiring increasingly greater traction on the plunger to remove the liquid to counteract the increasing pressure differential within the container. Further, this greater traction must be maintained until the needle is withdrawn from the diaphragm, in order to prevent the liquid from returning from the syringe into the container.

Efforts to design a pierceable diaphragm devoid of the above disadvantages have not been successful to date.

SUMMARY OF THE INVENTION

The invention comprises a pharmaceutical container of the pierceable diaphragm type which requires no initial injection of air into the container interior and which does not create a pressure differential within the container as the pharmaceutical is withdrawn.

In its broadest aspect, the invention comprises a pharmaceutical container of the pierceable diaphragm type for storing medication in fluid form for withdrawal when required, the container including a housing having a wall structure with an opening and a bottom seal, preferably integrally formed with the housing wall structure. The wall structure and the bottom seal together define an inner volume for the container.

A pierceable diaphragm is sealingly positioned within the housing opening, the diaphragm having one or more fluid check valves preferably integrally formed therein, each check valve affording one way fluid communication from ambient toward the inner volume of the container when the fluid pressure in the inner volume falls below ambient.

A protective cover is received over the diaphragm, and a fluid path means extends between an opening in the protective cover and the one or more check valves to promote air flow therebetween. In one embodiment, the fluid path means comprises a channel formed in the upper surface of the diaphragm and extending between a central opening in the protective cover and the diaphragm check valve or the plurality of check valves. In another embodiment, the fluid path means comprises a spacer member positioned between the protective cover and the diaphragm, the spacer member alternately comprising a screen-like meshed article or a series of projections extending from the top surface of the diaphragm.

In another embodiment, the protective cover is provided with a number of openings in at least partial registration with the diaphragm check valves, and a removable seal is placed over the protective cover to seal the cover openings until the container is ready for use. In this embodiment, the protective cover openings are substantially arcuate in shape.

The integral check valve formed in the diaphragm preferably comprises an inwardly tapering wall portion terminating in a self-sealing opening, the check valve opening being sealed when the inner volume fluid pressure is no less than ambient and the tapering wall portion being sufficiently flexible to permit unsealing of the check valve opening when the inner volume pressure is less than ambient by some amount.

In one specific embodiment of the invention, the seal is a cap-like structure having a peripheral wall portion with an inner diameter dimensioned to be received by the peripheral wall portion of the cover. The confronting wall portions of the cover and the seal preferably include a complementary detent portion to assist in retaining the seal on the cover. The seal may further include mechanically weakened sections of the peripheral wall portion to promote removal of the seal by fracturing of some of the weakened sections. The seal preferably includes a graspable laterally extending tab portion.

In use, the seal (in those embodiments provided with a seal) is removed and a syringe needle is inserted through an exposed portion of the diaphragm into the inner volume of the container and into the fluid medication contained therein. The syringe plunger is retracted by the user thereby starting the flow of fluid through the syringe needle and into the syringe. As the fluid is withdrawn from the inner volume of the container, the internal volume fluid pressure begins to drop below ambient until the diaphragm check valve(s) open in response to the pressure differential across the diaphragm. Once the required amount of fluid is withdrawn from the container, the syringe needle is withdrawn and the check valve(s) return to the sealed position once the pressure differential drops.

The invention eliminates the disruptive effect of suction flexing the diaphragm, and also eliminates any need to initially pressurize the inner volume of the container prior to withdrawal of the fluid medication. Since the negative pressure which develops within the inner volume is insufficient to mechanically distort the diaphragm, structural failure of this element due to repeated flexing is eliminated. Further, the absence of any need to pressurize the inner volume of the container eliminates any prospect of the fluid medication being forced out of the container and injuring the user.

For a fuller understanding of the nature and advantages of the invention, reference should be had to the ensuing detailed description taken in conjunction with the accompanying drawings.

DESCRIPTION OF THE PREFERRED EMBODIMENTS

Figure 1:
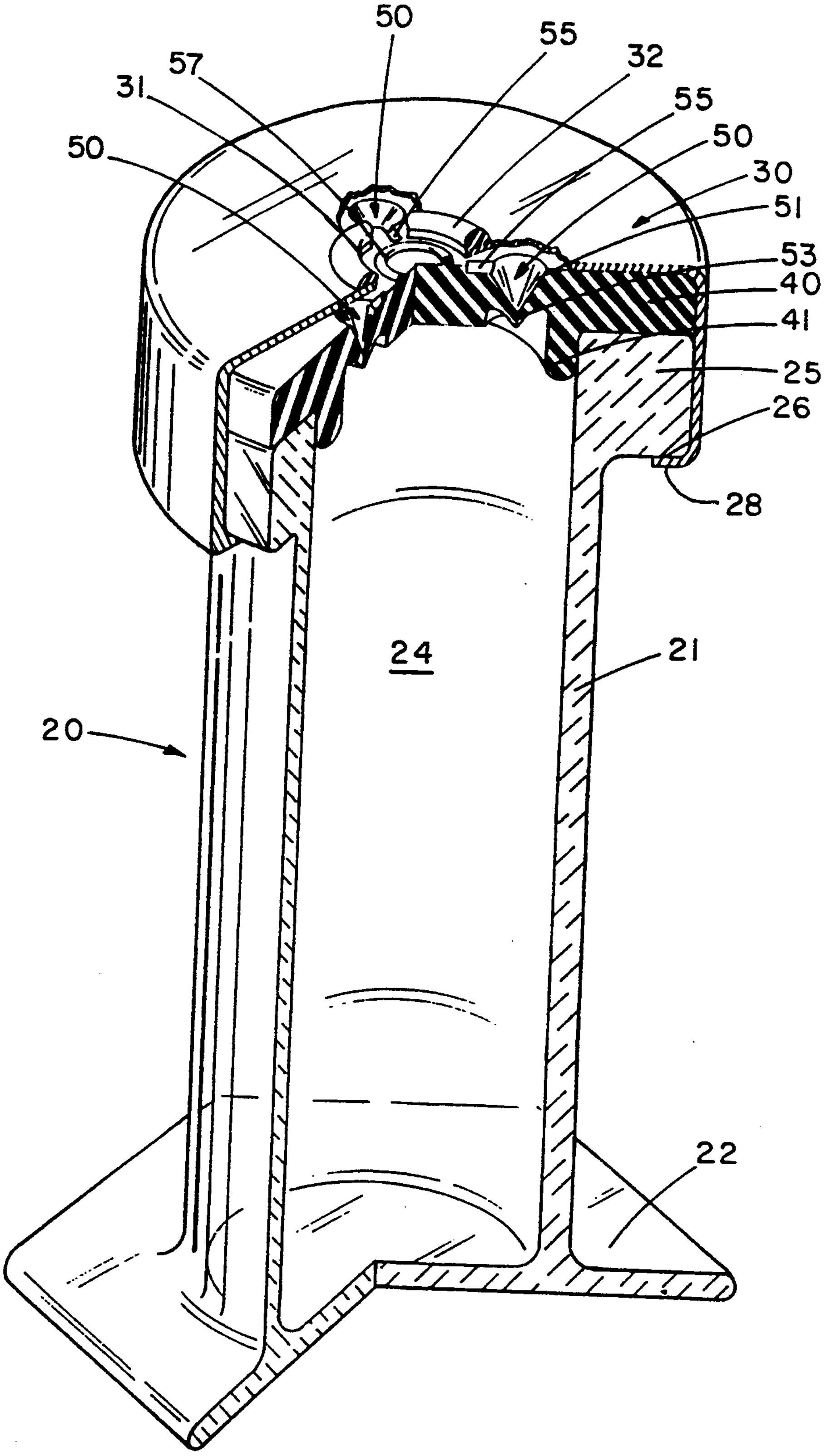
FIG. 1 is a partially cut-away prospective view of a first embodiment of the invention.
Figure 2:
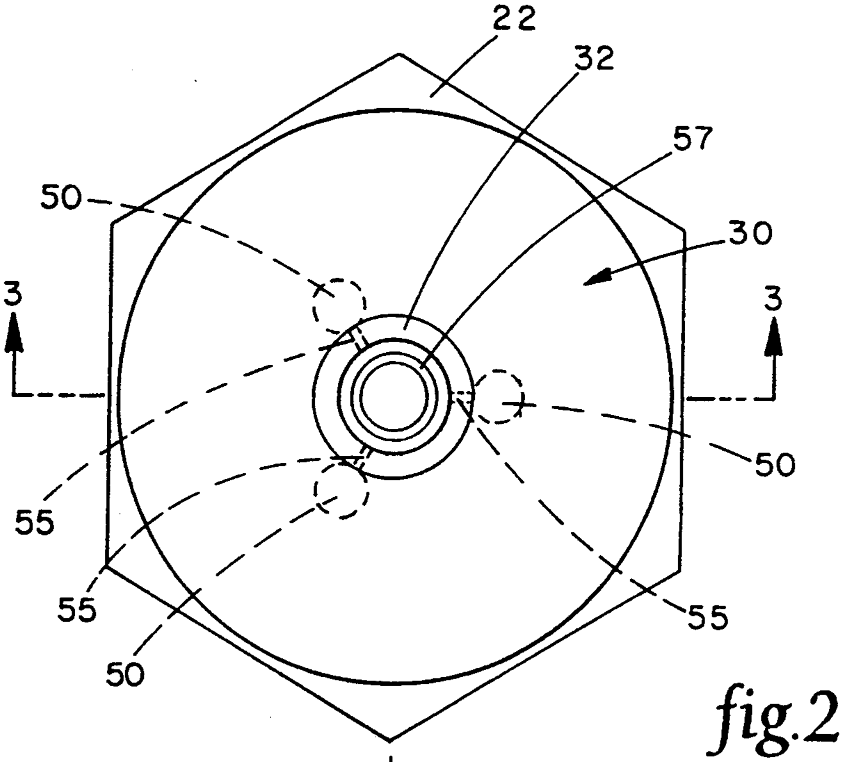
FIG. 2 is a top plan view of the embodiment of FIG. 1.
Figure 3:
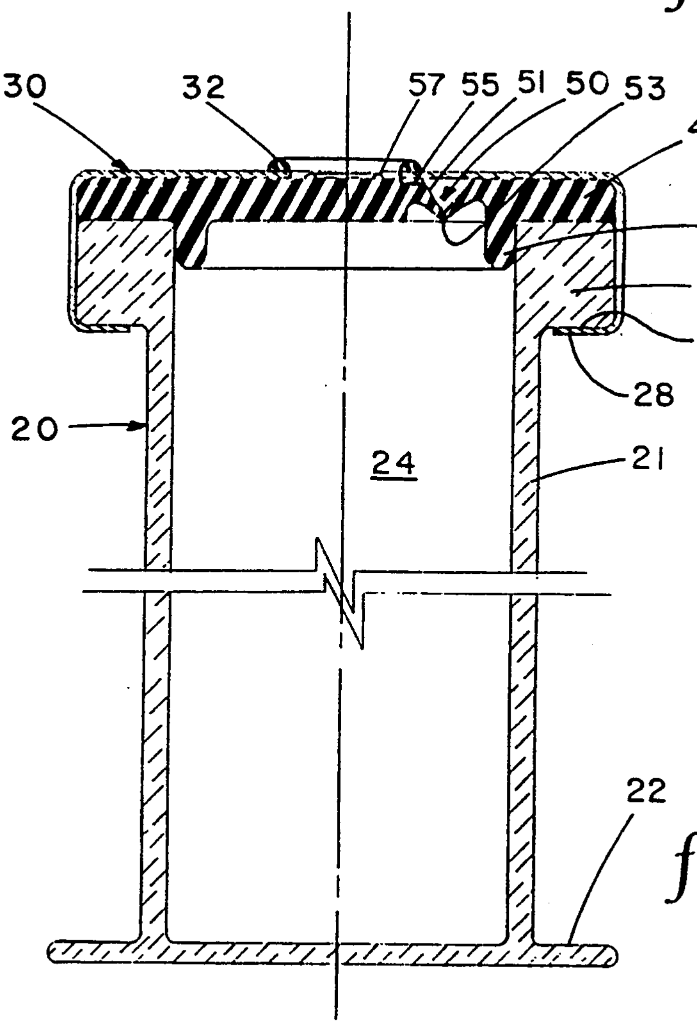
FIG. 3 is a sectional view taken along lines 3—3 of FIG. 2.

Turning now to the drawings, FIGS. 1–3 illustrate a first embodiment of the invention. As seen in these Figs., a container generally designated with reference numeral 20 has a longitudinally extending cylindrical wall 21 integrally formed with a base portion 22 to provide an internal volume 24 for containing a liquid medication. Wall structure 21 and base 22 may be fabricated from any suitable material, such as glass, polycarbonate plastic material or any other relatively inert material which is non-reactive with the medication to be contained. The upper portion of wall structure 21 terminates in an outwardly extending flange portion 25 providing a lower abutment edge 26 for engagement with the lower inwardly extending edge portion 28 of a protective cap 30. Cap 30 is preferably fabricated from soft aluminum. In the embodiment of FIGS. 1–3, cap 30 has a central opening 31 surrounded by a circular ridge 32 serving as a target indicator for assisting the user in inserting a syringe needle in the manner described below.

Positioned between flange 25 and cap 30 is a pierceable diaphragm generally designated with reference numeral 40. Diaphragm 40 has a lower lip portion 41 received in the upper end of wall structure 21 and forming a fluid seal therewith to provide closed containment for any medication within inner volume 24. Diaphragm 40 has a peripheral wall portion geometry which is conformable with the geometry of flange 25 and cap 30 so as to be permanently retained in the position illustrated in the Figs. Integrally formed in diaphragm 40 are a plurality of check valve portions generally designated with reference numeral 50. Each check valve portion 50 comprises a tapered wall portion 51 which tapers inwardly from the upper surface of diaphragm 40 toward inner volume 24. Wall surface 51 terminates at the lower end thereof in an opening or slit 53 which is normally closed whenever the fluid pressure within inner volume 24 is equal to or greater than ambient pressure outside container 20. When the pressure, within inner volume 24 drops below ambient by some threshold amount, the opening 53 is unsealed by the ambient fluid pressure, thereby providing an open fluid path through diaphragm 40. Since the opening 53 is only unsealed under these pressure differential conditions, the only possible fluid path flow is inwardly through diaphragm 40 into internal volume 24.

Also integrally formed in diaphragm 40 are a fluid path channels 55 extending from central opening 31 in protective cap 30 to check valves 50. Channels 55 provide a fluid path from ambient to the entrance of check valves 50 to promote fluid flow through the check valves 50 into inner volume 24. Diaphragm 40 is also provided with a circular ridged central portion 57 serving as a target or aiming indicator to facilitate use of the container 20 in combination with a needle syringe in the manner described below.

Diaphragm 40 is preferably fabricated from any suitable self-healing material capable of providing a tight fluid seal with wall structure 21 and capable of being provided with the check valves as shown. By "self-healing" is meant the ability to self-seal a needle puncture after the needle is withdrawn. Suitable materials for use in fabricating diaphragm 40 are butyl rubber, latex and silicone. Other materials will occur to those skilled in the art.

Figure 4:
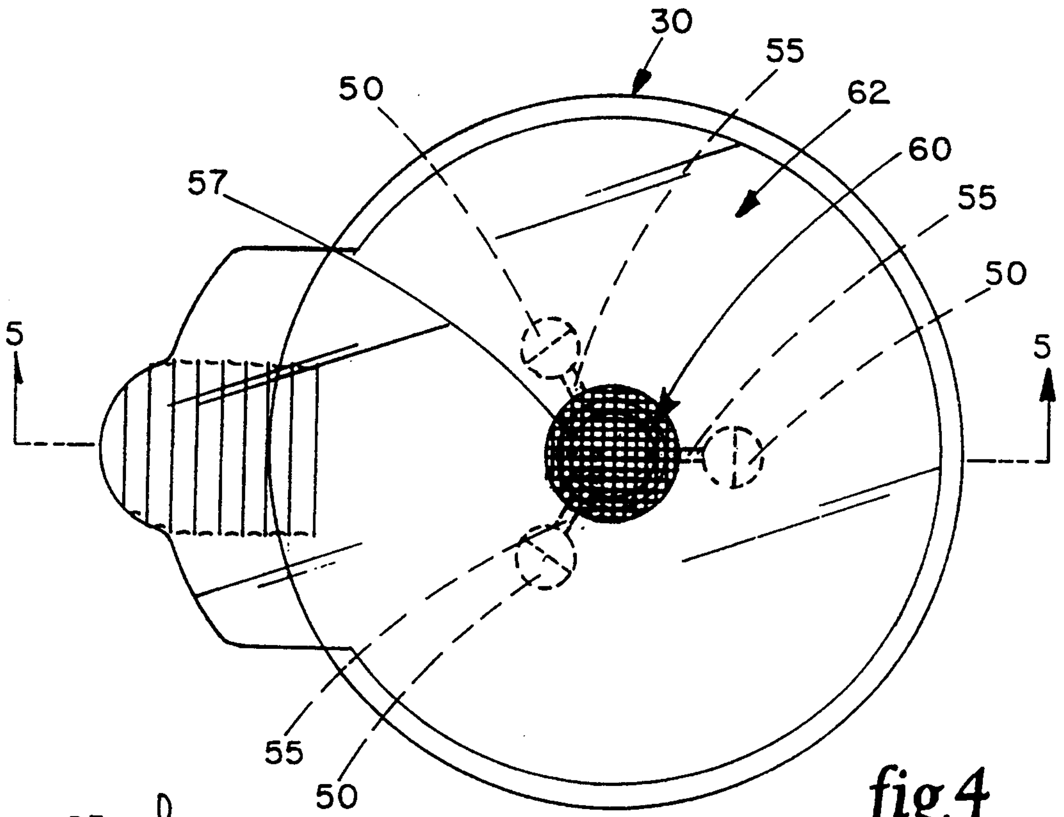
FIG. 4 is a top plan view of an alternate embodiment of the invention.
Figure 5:
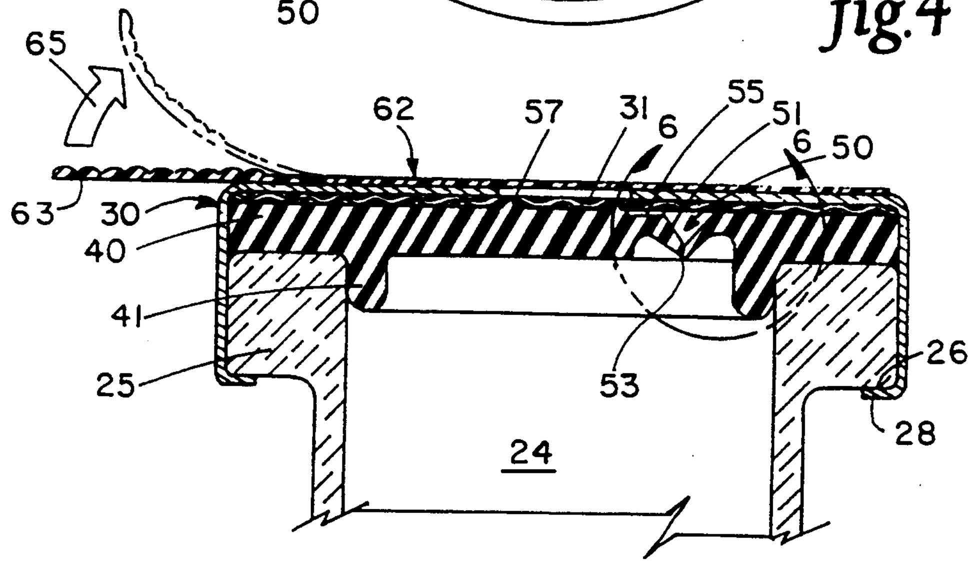
FIG. 5 is a sectional view taken along lines 5—5 of FIG. 4 of the upper portion of the FIG. 4 embodiment.
Figure 6:
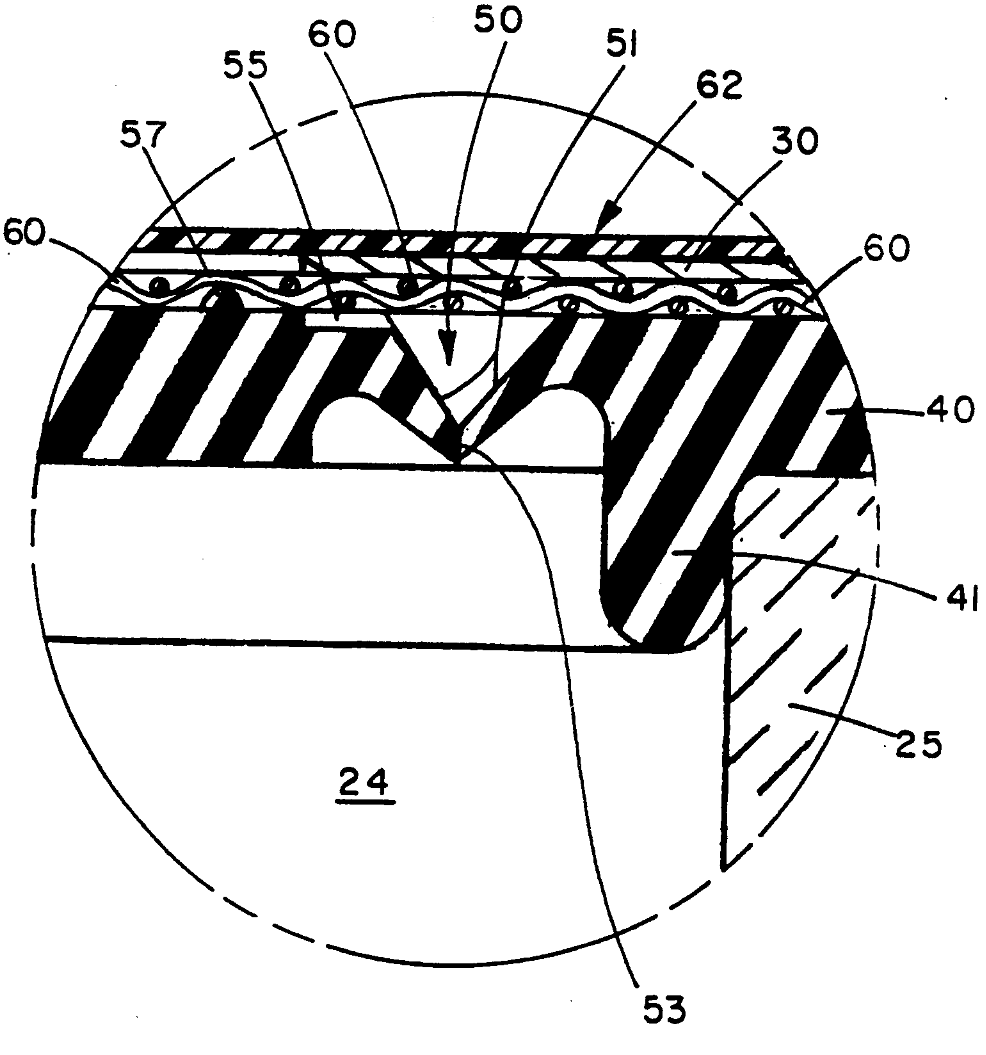
FIG. 6 is an enlarged detail view of a portion of FIG. 5 designated with double ended arrow 6—6.

FIGS. 4–6 illustrate another embodiment of the invention employing a removable seal for protective cap 30 and a different structure for providing the fluid channel paths from ambient to the inlet of the check valves. As seen in these Figs., a screen member 60 fabricated from a plastic or wire material is installed between the upper surface of diaphragm 40 and the inner surface of the top portion of protective cap 30. A flexible cover seal 62 having a laterally extending tab portion 63 is removably adhered to the top surface of protective cap 30 using any suitable adhesive, such as pressure sensitive acrylic. Seal 62 is fabricated from a thin flexible sheet-like material, such as Mylar, polypropylene, or polyethylene, and is designed to cover the central opening 31 in protective cover 30 when seal 62 is installed as shown in the Figs. Seal 62 can be removed, when necessary, by grasping the tab portion 63 and lifting in the direction designated with arrow 65. Once seal 62 is removed, the central opening in protective cap 30 is exposed to ambient and the undulating nature of the individual strands of the screen 60 provides additional free volume in the fluid path between the central opening 31 in protective cap 30 and the check valves 50. In particular, the under surface of cap 30 is spaced away from the upper surface of diaphragm 40 in this embodiment by the woven structure of screen 60 (see FIG. 6).

Figure 7:
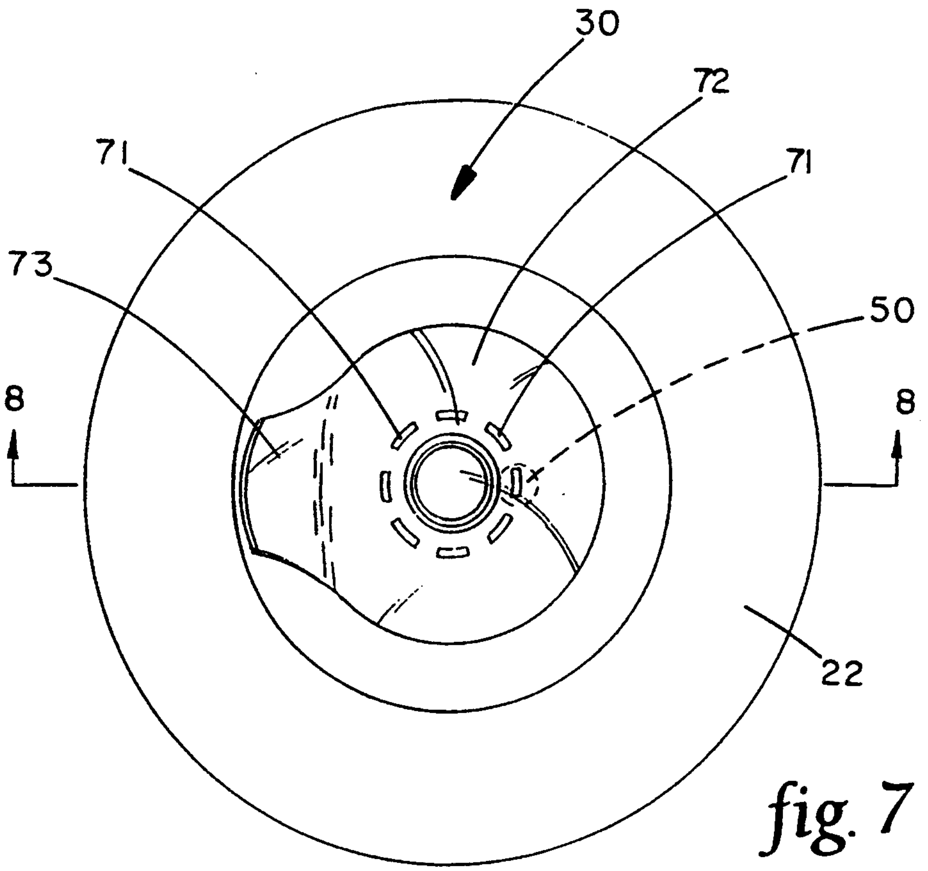
FIG. 7 is a top plan view of an alternate embodiment of the invention.
Figure 8:
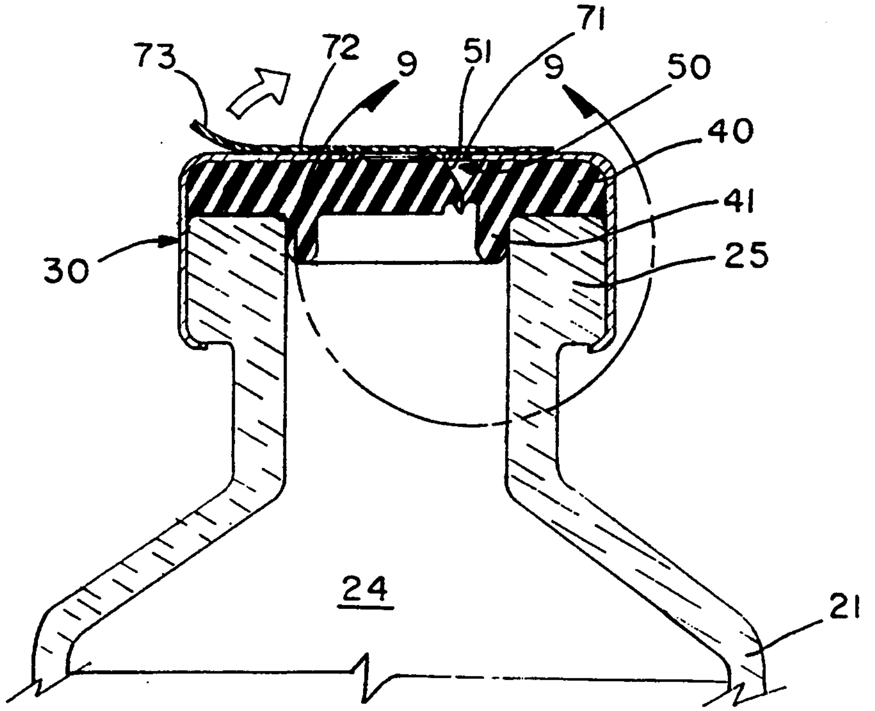
FIG. 8 is a sectional view taken along lines 8—8 of FIG. 7 of the upper portion of the embodiment of FIG. 7.
Figure 9:
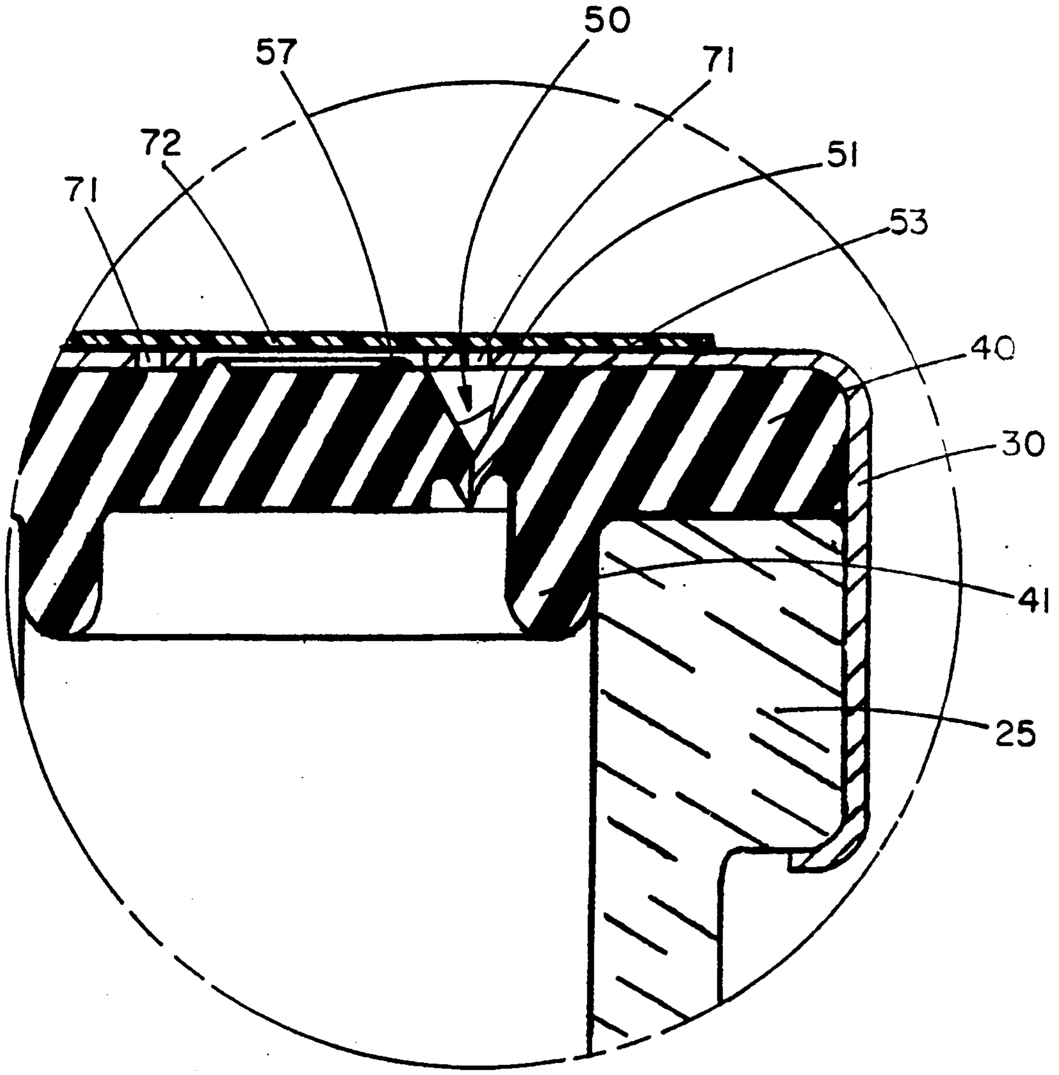
FIG. 9 is an enlarged detail view of the portion of FIG. 8 designated with double ended arrow 9—9.

FIGS. 7–9 illustrate still another embodiment of the invention employing a seal for protective cap 30 and a different fluid path arrangement. As seen in these Figs., protective cap 30 is provided with a series of arcuate openings 71, at least some of which are located over the single check valve 50 illustrated in these Figs. In this embodiment, the tab portion 73 of seal 72 terminates inwardly of the outer edge of cap 30. Also, base portion 22' is round as illustrated in FIG. 7. In use, when seal 72 is removed, the arcuate apertures 71 are uncovered and permit the flow of air therethrough to the inlet of the check valve 50.

Figure 10:
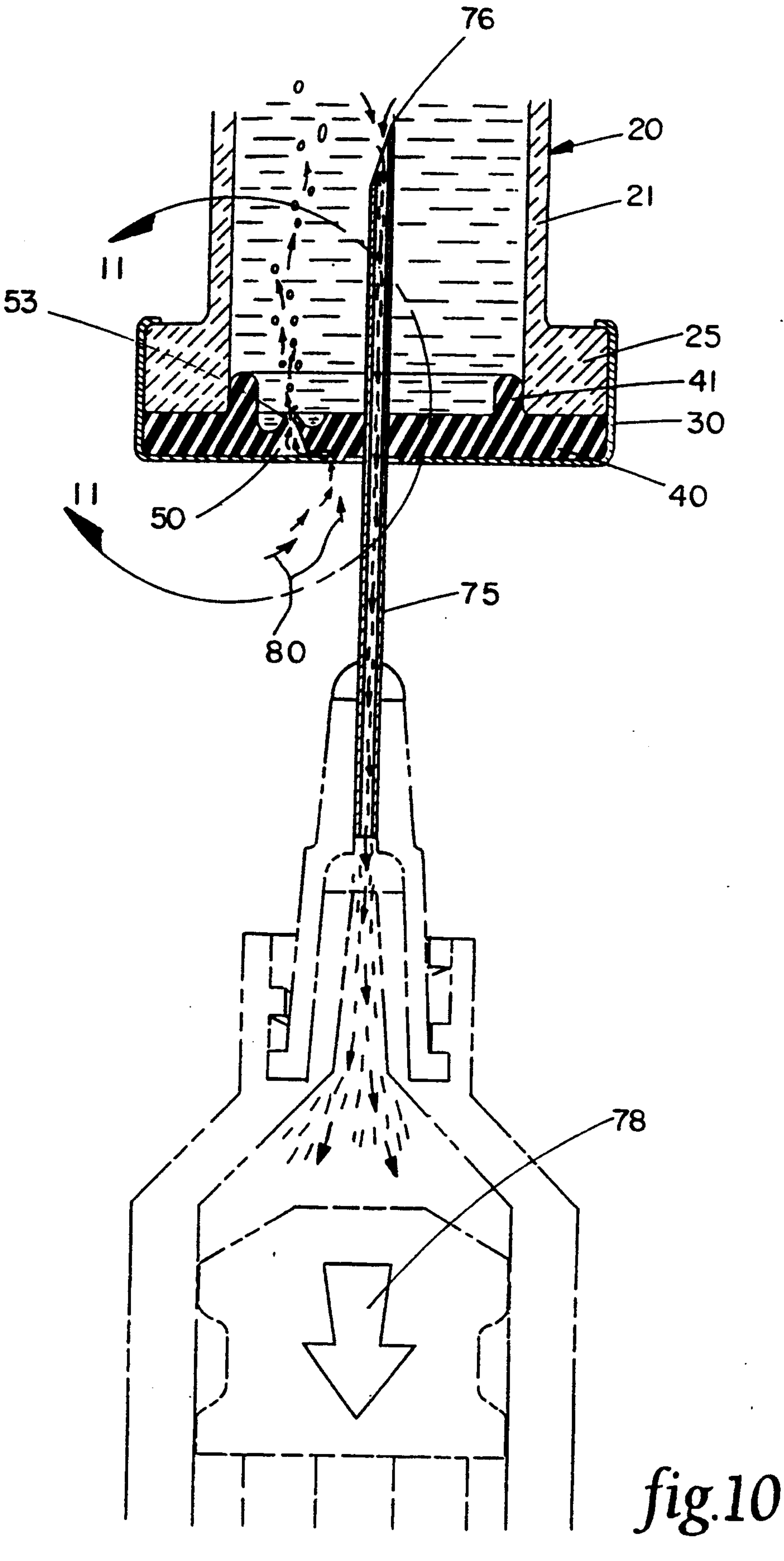
FIG. 10 is a schematic view showing a portion of the FIG. 4 embodiment in combination with the needle end of a syringe.
Figure 11:
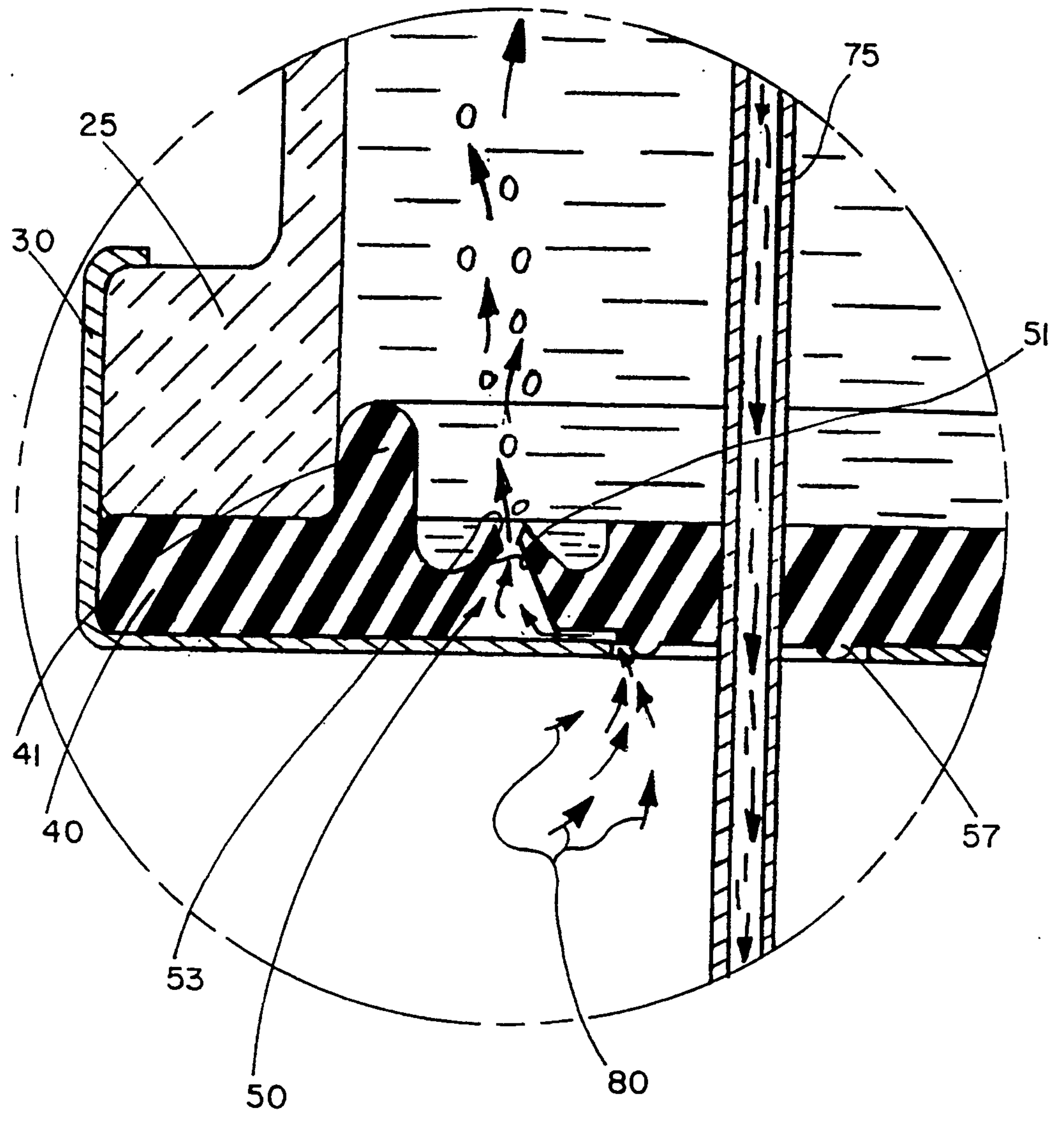
FIG. 11 is an enlarged detail view of the region designated by double ended arrow 11—11 of FIG. 10.

FIGS. 10 and 11 illustrate use of the embodiment of FIGS. 4–6 with a needle syringe. In FIG. 10, the syringe itself is shown in phantom lines while the needle 75 is shown in full. As seen in these Figs., after removal of the seal 62 the distal end 76 of needle 75 is inserted through the diaphragm 40 at the central portion thereof within the target annulus 57. With the distal end 76 of needle 75 immersed in the liquid medication, the syringe is operated in the direction indicated by arrow 78 to draw liquid into the interior of needle 75 and the interior of the syringe. As liquid is withdrawn, the pressure within container 20 drops, thereby permitting the air to flow through the check valve 50 in the direction indicated by arrows 80 from ambient to the interior of container 20. After sufficient liquid has been withdrawn, the fluid pressure within container 20 will rise to a value at which the check valve 50 reseals thereby stopping the flow of any more air into container 20 and also preventing the escape of any liquid through the check valve 50. Significantly, should the user force the syringe plunger in the reverse direction to pressurize the interior of container 20, check valve 50 remains sealed to prevent the escape of any liquid therethrough.

Figure 12:
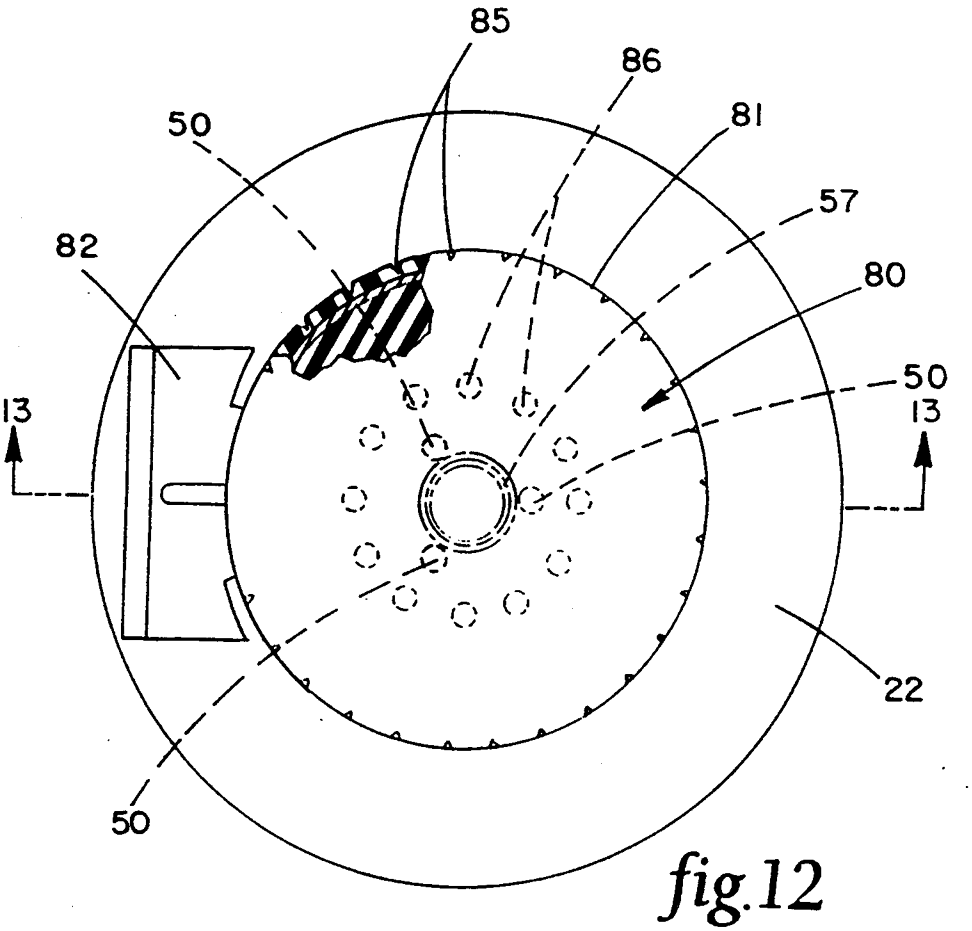
FIG. 12 is a top plan view of another embodiment of the invention.
Figure 13:
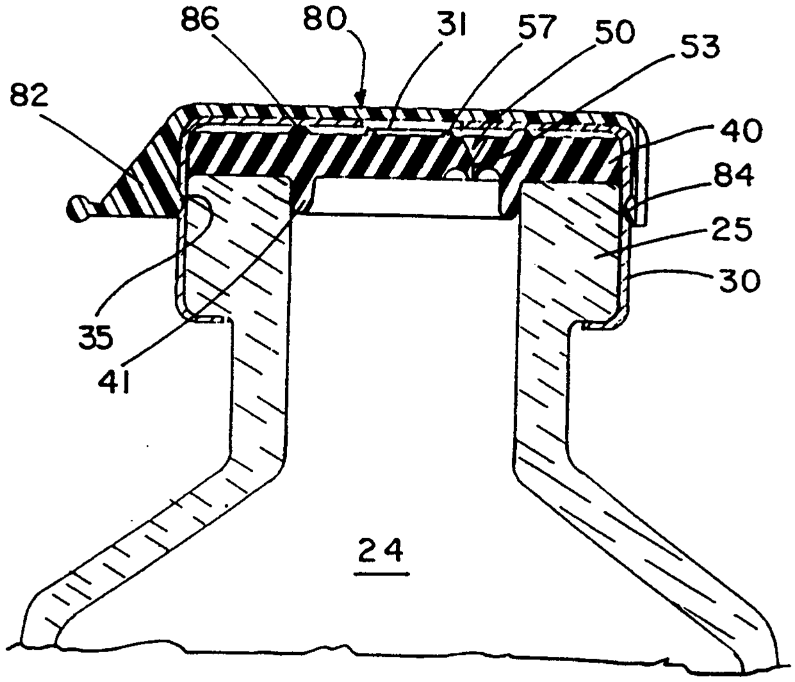
FIG. 13 is a sectional view taken along lines 13—13 of FIG. 12 showing the upper portion of the FIG. 12 embodiment.

FIGS. 12 and 13 illustrate still another embodiment of the invention in which the seal is in the form of a deformable member having a downwardly depending peripheral wall portion 81 with a thickened laterally extending tab portion 82. The inner surface of peripheral wall portion 81 and tab portion 82 are provided with a detent 84 illustrated as a ridge extending inwardly of seal 80. Protective cap 30 is also provided with a detent portion illustrated as a groove 35 formed in the sidewall portion thereof. As will be apparent to those skilled in the art, the arrangement of ridge 84 and groove 35 may be reversed, if desired so that ridge 84 is formed on the sidewall of cap 30 and groove 35 is formed in the inner surface of seal 80. In such an arrangement, the ridge 84 will extend outwardly into the inwardly facing groove 35. The positive detent afforded by elements 35, 84 can be overcome by grasping tab portion 82 of seal 80 and removing the seal in a conventional manner. In the embodiment shown in FIGS. 12 an 13, removal of seal 80 is assisted by providing weakening scores 85 along the peripheral wall portion 81 of seal 80. Preferably, scores 85 are sufficiently deep to permit the peripheral wall portion 81 to fracture if sufficient force is supplied to tab portion 82.

The embodiment of FIGS. 12 and 13 also includes a plurality of protrusions 86 integrally formed in the upper surface of diaphragm 40 and extending upwardly as viewed in FIG. 13. Protrusions 86 bear against the inner surface of protective cap 30 and provide additional volume between elements 30 and 40 to promote the flow of air from ambient through the central opening 31 in cap 30 toward check valves 50 in diaphragm 40.

As will now be apparent, the invention provides a pharmaceutical container which requires no initial pressurization and which renders the withdrawal of liquids from the container relatively safe and simple. The lack of developing back pressure within the pharmaceutical container fabricated according to the invention enables smooth withdrawal of the liquid without the need for increasing pressure on the syringe plunger to ensure steady withdrawal of the liquid medication. Also, the invention is relatively simple in construction, and easy to assemble.

While the above provides a full and complete disclosure of the preferred embodiments of the invention, various modifications, alternate constructions and equivalents may be employed as desired. For example, while base 22 has been illustrated and described as being integrally formed with wall structure 21, these elements may be formed as individual elements and sealed together, if desired. In addition, the check valves 50 need not be uniformly distributed about the center of diaphragm 40, but may assume other appropriate locations, such as staggered distances from the center of the diaphragm. In addition, the specific materials identified above for the respective elements of the preferred embodiments are not intended to be limiting but merely exemplary. Also, check valves having other geometry than illustrated valves 50 may be employed, such as trough-shaped walls with an aperture slit. Further, although container 20 has been described and illustrated as having right circular cylindrical geometry, other shapes may be employed, if desired. Moreover, detent portions 35, 84 may assume other shapes, e.g., ball and socket detents, if desired. Therefore, the above should not be construed as limiting the invention, which is defined by the appended claims.

What is claimed is:

1. A pharmaceutical container of the pierceable diaphragm type for storing medication in fluid form for withdrawal when required, said container comprising:

a housing having a wall structure with an opening and a bottom, said wall structure and said bottom together defining an inner volume;

a pierceable diaphragm sealingly positioned in said opening, said diaphragm having an outer surface and at least one fluid check valve affording one way fluid communication from an ambient atmosphere toward said inner volume when said inner volume has a fluid pressure less than the fluid pressure of the ambient atmosphere, the outer surface having a needle-pierceable region;

a protective cover covering said check valve while leaving at least a portion of the needle-pierceable region exposed; and a fluid pathway defined between the cover and the outer surface fluidly coupling the ambient atmosphere with said check valve.

2. The invention of claim 1 wherein said bottom is integrally formed with said wall structure of said housing.

3. The invention of claim 1 wherein said check valve is integrally formed with said diaphragm.

4. The invention of claim 1 wherein said check valve comprises an inwardly tapering wall portion integrally formed in said diaphragm and terminating in a self-sealing opening, said check valve opening being sealed when the inner volume fluid pressure is no less than the ambient pressure, said inwardly tapering wall portion being sufficiently flexible to permit unsealing of said opening when the inner volume pressure is less than the ambient pressure by some amount.

5. The invention of claim 1 wherein said diaphragm is fabricated from a self-healing material.

6. The invention of claim 5 wherein said self-healing material is butyl rubber.

7. The invention of claim 1 wherein said fluid pathway includes a spacer member positioned between said cover and said diaphragm.

8. The invention of claim 7 wherein said spacer member is fabricated from a screen-like material.

9. The invention of claim 7 wherein said spacer member comprises a protrusion extending from said diaphragm toward said cover.

10. The invention of claim 1 wherein said check valve is offset from a central portion of said diaphragm; and wherein said diaphragm partially defines said fluid pathway, said fluid pathway extending from said check valve toward said needle pierceable region.

11. The invention of claim 10 wherein said fluid pathway comprises a groove formed in the outer surface of said diaphragm.

12. The invention of claim 4 wherein said diaphragm is provided with a plurality of check valves.

13. The invention of claim 12 wherein said plurality of check valves is distributed about the needle-pierceable region of the outer surface of said diaphragm.

14. The invention of claim 1 further including a seal removably positioned on said cover for sealing the fluid pathway and preventing ambient atmosphere flow toward said check valve when said seal is installed.

15. The invention of claim 14 wherein said seal includes a tab portion.

16. The invention of claim 15 wherein said tab portion extends laterally of said wall structure.

17. The invention of claim 16 wherein said cover has a peripheral wall portion; and wherein said seal has a peripheral wall portion with an inner diameter dimensioned to be received by said peripheral wall portion of said cover.

18. The invention of claim 17 wherein said wall portions include a complementary detent portion.

19. The invention of claim 17 wherein said peripheral wall portion of said seal is provided with mechanically weakened sections to promote removal of said seal.

20. A pharmaceutical container of the pierceable diaphragm type for storing medication in fluid form for withdrawal when required, said container comprising:

a housing having a wall structure with an opening and a bottom, said wall structure and said bottom together defining an inner volume;

a diaphragm sealingly positioned in said opening, said diaphragm having an outer surface and at least one fluid check valve affording one way fluid communication from an ambient atmosphere toward said inner volume when said inner volume has a fluid pressure less than the fluid pressure of the ambient atmosphere, the outer surface having a needle-pierceable, self-healing region;

a protective cover covering said check valve, the cover including an open needle access region aligned with at least a portion of the needle-pierceable region to leave said needle-pierceable region exposed to the ambient atmosphere;

a spacer member positioned between said cover and said diaphragm;

a fluid pathway, defined by the spacer member and the outer surface of the diaphragm, fluidly coupling the needle-pierceable region and said check valve;

a seal removably positioned on said cover for covering the needle access region to prevent ambient atmosphere flow through the needle access region and the fluid pathway and to said check valve when said seal is installed.

* * * * *